US00RE34632E

United States Patent [19]

Berggren et al.

[11] E Patent Number: Re. 34,632

[45] Reissued Date of Patent: Jun. 7, 1994

[54] DEVICE AT ARTIFICIAL JOINTS

[75] Inventors: Anders Berggren, Linkoping; Hakan Rohman, Mantorp, both of Sweden

[73] Assignee: Unilink, Inc., Centreville, Va.

[21] Appl. No.: 910,825

[22] Filed: Jul. 7, 1992

Related U.S. Patent Documents

Reissue of:

[64] Patent No.: 5,061,288
Issued: Oct. 29, 1991
Appl. No.: 548,958
Filed: Aug. 21, 1990

[30] Foreign Application Priority Data

Jan. 28, 1988 [SE] Sweden ..... 8800274.6

[51] Int. Cl.[5] ..... A61F 2/30

[52] U.S. Cl. ..... 623/18; 623/23

[58] Field of Search ..... 623/16, 18, 23; 15/159.1, 162, 164, 165, 206, 207; 433/173, 175, 176, 201.1

[56] References Cited

U.S. PATENT DOCUMENTS 2,339,123 1/1944 Volckening ..... 15/207
4,114,504 9/1978 Koregelos ..... 15/164
4,671,768 6/1987 Ton ..... 433/201.1
4,681,590 7/1987 Tansey ..... 623/23

FOREIGN PATENT DOCUMENTS 3613657 11/1987 Fed. Rep. of Germany .
728855 5/1980 U.S.S.R. ..... 433/176

OTHER PUBLICATIONS

Adell et al., "A 15-year Study of Osseointegrated Implants in the Treatment of the Edentulous Jaw," Int. J. Oral. Surg., 1981, 10:387–416.

Raveh et al., "Use of the Titanium-coated Hollow Screw and Reconstruction Plate System in Bridging of Lower Jaw Defects," J Oral Maxillofac Surg, 42:281–294, 1984.

*Primary Examiner*—Randy C. Shay
*Attorney, Agent, or Firm*—Woodcock, Washburn, Kurtz, Mackiewicz & Norris

[57] ABSTRACT

Fastening means for artificial joints including two titanium wires that are wound into a spiral and wherein the wires clamp a number of bristles between them that extend essentially radially outwards toward the interior of the bone. The bristles are a little bit too long for undisturbed insertion into the cavity of the bone and, thus they will be slightly turned backwards on insertion, thereby securing a very steady grip once inserted.

22 Claims, 3 Drawing Sheets

DEVICE AT ARTIFICIAL JOINTS

Matter enclosed in heavy brackets [ ] appears in the original patent but forms no part of this reissue specification; matter printed in italics indicates the additions made by reissue.

BACKGROUND OF THE INVENTION

It has been known for some time how to replace worn, or in other ways damaged, joints—for instance joints damaged by rheumatism, by removing a joint end from a bone and replacing this end with an artificial part. These artificial parts include a joint part and a connection part that is inserted into the cavity of the remaining bone. The fastening of the artificial part in the bone has been carried out in different way, for instance, the connection part has been threaded and/or cemented into the bone.

Presently available artificial parts have a number of drawbacks. Firstly, this method of fasteing is comparatively complicated and time consuming. Secondly, with time, great loads, for instance in the vicinity of knee joints and thigh bones, cause an increasing play between an artificial part and bone, which may require a replacement of the artificial part. Change of the artificial part normally involves the shortening of the bone to obtain adequate material in which to fasten the artificial part. After a few replacements of the artificial part, so little of the bone remains that the joint must be made rigid due to the lack of bone material.

A further drawback of the artificial parts known thus far is that the natural formation of blood vessels cannot occur within inner cavity of the bone, which presumably further reduces the life span of the mounting of the artificial part and, thus, of the artificial part itself.

SUMMARY OF THE INVENTION

Some objects of this invention are to solve the above mentioned problems and to provide a simple, useable, artificial part fastening or mounting that is easy to apply, that does not need to be exchanged, and that allows improved vascularization. Other and further objects and advantages will appear hereinafter.

These objects may be achieved in accordance with the present invention by means of a supporting structure that is inserted into the axial cavity of the bone. This supporting structure is provided with bristles, fibers, loops, or the like, with such length that the combined diameter of the device is somewhat larger than the cavity in the bone, allowing at least some of the bristles, fibers, loops, or the like to retain a certain pretension at mounting. In other words, when the fastening element is inserted into the hollow of the bone, the bristles are bent somewhat, thereby causing greater resistance against withdrawal than against insertion. It will in fact be practically impossible to withdraw the fastening element. Preferably the number of bristles, fibers or the like is very large. In this way extensive contact between bone and the artificial part fastening element is obtained simultaneously as an adaption is automatically made to possible irregularities on the inside of the bone.

Furthermore, by fabricating the bristles, fibers, or loops in titanium, the bone and the artificial part fastening element will grow together and with time will become integrated. Bleeding and vascularization can take place between the bristles, fibers or loops. Furthermore, it is also possible to make the supporting structure more or less porous or open. Since the tensions are less as you go further into the bone, the fastening element can be more open or have fewer bristles, further within the bone. The length of the bristles, and the density thereof, are primarily governed by the forces that have to be transferred. Therefore, the density of the bristles need not necessarily be the same over the entire length of the fastening element.

If bristles of titanium are used, many thin bristles can be used in view of the hard, stiff character of titanium. In the alternative, titanium-containing alloys coated by titanium can be used. It is also possible to use plastic materials coated with titanium.

The bristles may initially be directed radially or possibly somewhat rearward. It is also possible that only some of the bristles are so directed.

The supporting structure need not necessarily be rigid, but may allow a certain elasticity that may preferably be calculated to coincide with that of the bone so that no tension peaks are developed in the force transfer back and forth.

By means of the invention, an immediate sturdy grip is obtained in the bone, preventing the mounted artificial part from loosening. With the use of titanium, the device is prevented from working loose over time since the contact surface is great and, thus, the specific load small.

It should be observed that the fastening means described above can also be used for the joining of broken bones.

Further details and advantages of the invention will become apparent from the following description of a preferred embodiment and the claims.

DETAILED DESCRIPTION OF PREFERRED EMBODIMENTS

Figure 1:
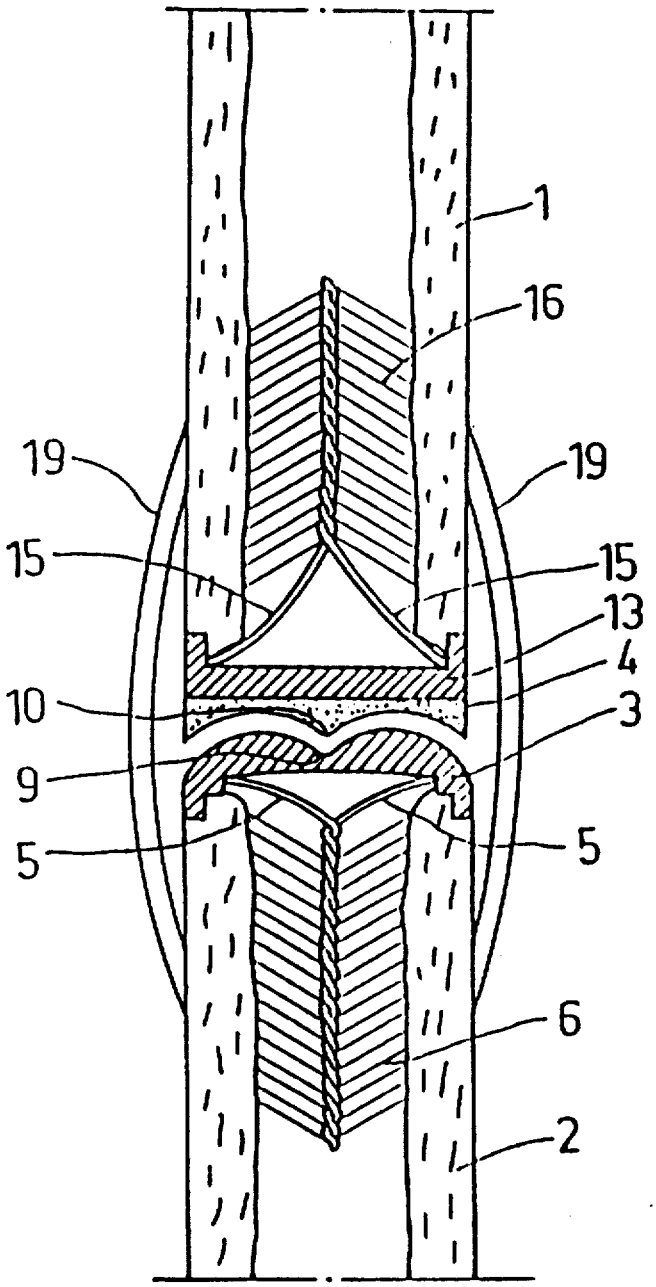
FIG. 1 shows a cross-section of a joint with the device of the present invention as seen from the front.
Figure 2:
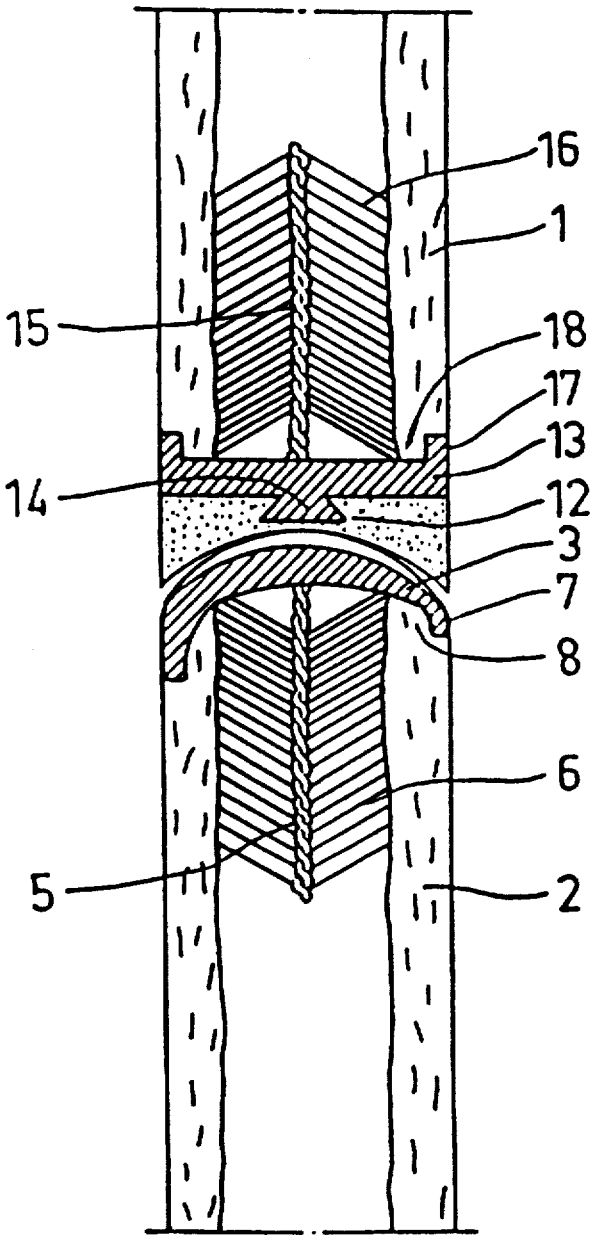
FIG. 2 shows the same joint and device of FIG. 1 in cross section from the side.
Figure 3:
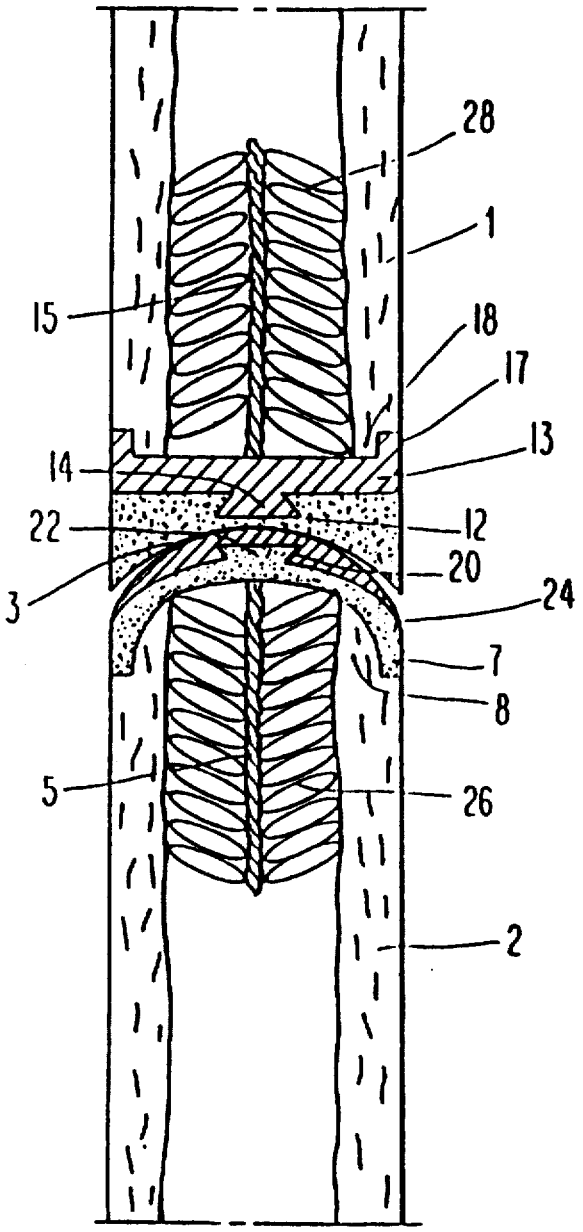
FIG. 3 shows a cross-section of a joint with an alternative embodiment of the device of the present invention from the side.

The artificial joint shown in the drawings (where like numbers designate like elements) includes a bowl or concave joint part 4 and a ball joint part 3, each fastened in a bone, I and 2 respectively. The lower part, the ball part 3, is welded to two wires 5 of titanium that, from diametrical peripheral fastening points, extend toward each other, then continue by winding around each other. In FIGS. 1 and 2, between the spirals of these two wires 5, thin threadlike bristles 6, also of titanium, are clamped. FIG. 3 illustrated the use of loops 26 as an alternative to the bristles 6 of FIGS. 1 and 2.

The bristles 6, or loops 26 are of a length such that they, on insertion into the bone 2, will be bent somewhat upwards. This means that they will not exert any particular resistance against their introduction into the bone. However, the resistance against possible attempts to withdraw the artificial joint part from the bone will be very great. By using a large number of bristles or loops, a good fastening against turning of the artificial joint part relative to the bone is achieved.

The ball joint part 3 has a circumferential downwards protruding flange 7 gripping around the bone 2 on its corresponding shaped end 8. In this way, the artificial joint part will be locked against possible tilting, with the bristles and the titanium wire pressing the ball joint part against the bone 2.

In one embodiment, the interior of the ball joint 3 can be filled with silicone at the mounting. In the alternative, the interior can be entirely empty. By using pure titanium or titanium alloys or other materials coated with titanium, or perhaps ever other materials that can grow together with the bone, over time an integration is achieved. In this way, not only is there an immediate, sturdy attachment, but there is also a lasting attachment to the bone.

The upper joint bowl part or concave part 4 has a shape corresponding to the shape of the ball joint part 3 so that an angular movement is possible. The surfaces facing each other are usually cylindrical or spherical surfaces where the lower ball joint part 3 has a waist or groove 9 into which a protrusion or ridge 10 on the upper bowl joint part can grip to provide an increased resistance against turning and sideways dislocation. By proportioning the interrelated length of groove and the ridge angle, stops for the joint can be achieved. The upper bowl joint part 4 is not made of titanium, but is made of a synthetic material that affords negligible friction against titanium. An example of this is high density polyethylene (HDP) that has proven to be compatible with human tissues. In the bowl part 4, a dove tail groove 12 extends sideways and into this grips a correspondingly shaped dove tail 14 that, in turn, is part of a titanium plate 13. Preferably, the titanium plate 13 and the joint bowl part 4 of HDP are provided with snap means so that the lateral location, when ideally situated, is secured. Wires 15 are welded to the plate 13 and are then wound to a spiral that holds bristles 16, or loops 28 in the same way as has been described above for the lower ball shaped joint part 3. Also, the titanium disk or plate 13 is provided with a flange 17 gripping around a corresponding shaping 18 of the bone 1.

The use of a dove tail joint to join the joint bowl part 4 with its fastening means provides the advantage that the joint bowl part 4 can easily be exchanged if, for instance, after many years of use, the part becomes worn. The exchange can be accomplished through a procedure that is far easier and less complicated and time consuming than would be the case if it were necessary to exchange the entire artificial joint or artificial joint part.

Of course, the lower ball joint part 3 can also be made in a similar way to allow a change of a part subjected to wear, as shown in FIG. 3. This can, for instance, take place by use of a dove tail joint with the interlocation of a plastic part. Thus, a dove tail groove [29] *20* can extend sideways in the lower ball joint 3 and into this grips a correspondingly shaped dove tail 22 that, in turn, is part of a plastic plate 24. By using plastic for one half of the joint, and possibly as a joining element in the lower part, a certain elasticity against shock is achieved that reduces tensions in other joints as well as in the fastening of the artificial joint.

It should be observed that the flanges 7 and 17, and the corresponding shaping of the bone ends respectively, need not necessarily be exactly matched to the outer shape of the bone, but, instead, to facilitate working, it is possible to use flanges that are circular, for instance concentric with the axis of the wound titanium wires.

The joint has a ligament 19 on each side.

By means of the invention, an artificial joint or joint parts is realized for large as well as small joints that is very similar to the desired relationships of the original joint.

Since the fastening according to the invention in principle is, or can be made, elastic over its entire length, there will be no tension peaks where the artificial part ends, unlike many known artificial joint parts in which such tension peaks do occur.

Due to the improved fastening characteristics and the soft transference of forces from the artificial part to the bone, it is actually possible to make other types of replacements that have previously been impossible. Due to previously poor fastening characteristics, the artificial part has always had to be comparatively short in order to avoid having excessive torques exerted on the remaining bone part. With the invention, the remaining bone will not be subjected to forces greater than the bone originally could tolerate. Therefore, an artificial joint part according to the invention can be longer, thereby abolishing the previous necessity of bone shortening.

The drawings have shown the use of two wires for fastening the bristles. Of course, more than two wires can be used and it is also possible to use different types of supporting structure for carrying the bristles. For instance, the bristles can be fastened in a cast plastic structure.

If the stiffness of the supporting structure decreases towards the interior of the cavity, the transference of forces to and from the joint will take place without significant tension peaks.

In the above example, two wires have been used to secure or fasten the bristles, however, a greater number of bristles can also be used. Furthermore, if any other type of supporting structure is used, for instance a plastic structure, then a porous or open structure can also be employed.

Thus, a fastening means for artificial joints is disclosed. While embodiments and applications of this invention have been shown and described, it would be apparent to those of ordinary skill in the art that many more modifications are possible without departing from the inventive concepts herein. The invention, therefore, is not to be restricted except in the spirit of the appended claims.

What is claimed is:

1. An artificial joint for connecting [an upper bone having a cavity therein] *a first part* and a [lower] bone *part* having a cavity therein, said artificial joint comprising:

[an upper concave] *a* joint part having a [concave] *first* portion *comprising means for attaching said joint part to said first part* and *having* an opposite side;

[a lower ball joint part having a rounded portion and an opposite side oriented such that the rounded portion of the lower ball joint part fits within the concave portion of the upper concave joint part;]

a [pair of] support [structures, one] *structure* attached to the opposite side of the [upper concave] joint part and [one attached to the opposite side of the lower ball joint part, each of the support structures] having an end remote from [their respective] *the* joint [parts] *part* adapted for insertion and retention into [a] *the* cavity of [one of] said [upper and lower bones] *bone part* and holding means on [each] *the* support structure for holding such support structure in [a respective] *the* bone cavity, said holding means comprising a plurality of bristles, fibers, or loops extending from [a respective] *the support* structure only radially outwardly and toward [a respective] *the* joint part, wherein the length of at least a portion of the bristles, fibers, or loops is such that the outer diameter of such bristles, fibers, or loops as attached to the [respective] support structure in an untensioned state is adapted to exceed the diameter of the cavity in which it is to be inserted.

2. The artificial joint of claim 1 wherein [each of] said support [structures comprise] *structure comprises* a spiral of wound wires, said [bristle] *bristles*, fibers, or loops being clamped between the wound wires.

3. The artificial joint of claim 1 wherein one or more of the [lower ball] joint part, the support [structures] *structure*, and the bristles, fibers, or loops are comprised of titanium or titanium alloys.

4. The artificial joint of claim 1 wherein one or more of the [lower ball] joint part, the support [structures] *structure*, and the bristles, fibers, or loops are coated with titanium.

5. The artificial joint of claim 1 wherein the density of the bristles, fibers, or loops decreases towards the remote [ends] *end* of the support [structures] *structure*.

6. The artificial joint of claim 1 wherein said support [structures are] *structure is* comprised of a plastic.

7. The artificial joint of claim 1 wherein said support [structures decrease] *structure decreases* in stiffness towards the remote [ends] *end*

8. The artificial joint of claim [1] *22* wherein the rounded portion of the lower ball joint part has a groove into which a protrusion on the concave portion of the upper concave joint part fits to provide increased resistance against turning and sideways dislocation of the attached bones.

9. The artificial joint of claim [1] *22* wherein the upper concave joint part is comprised of a cup part having a concave side and an opposite side and a plate part attached to said opposite side of the cup part.

10. The artificial joint of claim 9 wherein the cup part of the upper concave joint part is comprised of a biocompatible material chosen to minimize friction with titanium.

11. The artificial joint of claim 9 wherein said cup part of the upper concave joint part is comprised of high density polyethylene.

12. The artificial joint of of claim 9 wherein said plate part of the upper concave joint part further comprises a flange extending away from the cup part and formed to grip the upper bone.

13. The artificial joint of claim 9 wherein said plate part of the upper concave joint part is comprised of titanium or titanium alloys.

14. The artificial joint of claim 9 wherein said plate part of the upper concave joint part is removably attached to the cup part to allow replacement of the said cup part.

15. The artificial joint of claim 14 wherein said plate part is removably attached by means of a dove tail ridge extending along said plate part in a direction perpendicular to the bending plane of said artificial joint that is inserted into a dove tail groove extending along the opposite side of said cup part in a similar direction.

16. The artificial joint of claim [1] *22* wherein said lower ball joint part further comprises a flange extending from the opposite side and formed to grip the lower bone.

17. The artificial joint of claim [1] *22* wherein said lower ball joint part is comprised of a rotator part having a rounded portion and an opposite side and a plate part attached to the opposite side of the rotator part.

18. The artificial joint of claim 17 wherein said plate part of said lower ball joint part is comprised of an elastic substance.

19. The artificial joint of claim 17 wherein said plate part of the lower ball joint part is removably attached to the rotator part to allow replacement of the said rotator part.

20. The artificial joint of claim 19 wherein said plate part of the lower ball joint part is removably attached by means of a dove tail ridge extending along said plate part in a direction perpendicular to the bending plane of said artificial joint that is inserted into a dove tail groove extending along the opposite side of said rotator part in a similar direction.

21. An artificial joint for connecting an upper bone having a cavity therein and a lower bone having a cavity therein, said artificial joint comprising:

an upper concave joint part comprised of a cup part, having a concave side with a protrusion therein and an opposite side, and a plate part removably attached to said opposite side of said cup part;

a lower ball joint part having a rotator part having a rounded portion with a groove therein and an opposite side, oriented such that the rounded portion of the lower ball joint part fits within the concave portion of the upper cancave joint part and the groove fits to the protrusion, and a plate part removably attached to the opposite side of the rotator part;

a pair of support structures, each comprised of a spiral of wound wires, one attached to the opposite side of the upper concave joint part and one attached to the opposite side of the lower ball joint part, each of the support structures having an end adapted for insertion and retention into a cavity of one of said upper and lower bones and holding means on each support structure for holding such support structure in a respective bone cavity, said holding means comprising a plurality of bristles, fibers, or loops extending from a respective structure only radially outwardly and toward a respective joint part, the length of the bristles, fibers, or loops being such that an outer diameter of the bristles, fibers, or loops as attached to the support structure in an untensioned state is adapted to exceed the diameter of the cavity in which it is to be inserted and the bristles, fibers, or loops are angled only radially downwardly from the support structure towards the joint parts and we adapted to be tensioned against the interior of the cavities; and wherein one or more of the plate part of the upper concave joint part, the rotator part, the plate part of the lower ball joint part, the wound wires, and the bristles, fibers, or loops is comprised of titanium or titanium alloys.

*22. An artificial joint for connecting an upper bone having a cavity therein and a lower bone having a cavity therein, said artificial joint comprising:*

*an upper concave joint part having a concave portion and an opposite side;*

*a lower ball joint part having a rounded portion and an opposite side oriented such that the rounded portion of the lower ball joint part fits within the concave portion of the upper concave joint part;*

*a pair of support structures, one attached to the opposite side of the upper concave joint part and one attached to the opposite side of the lower ball joint part, each of the support structures having an end remote from their respective joint parts adapted for insertion and retention into a cavity of one of said upper and lower bones and holding means on each support structure for holding such support structure in a respective bone cavity, said holding means comprising a plurality of bristles, fibers, or loops extending from a respective structure only radially outwardly and toward a respective joint part, wherein the length of at least a portion of the bristles, fibers, or loops is such that the outer diameter of such bristles, fibers, or loops as attached to the respective support structure in an untensioned state is adapted to exceed the diameter of the cavity in which it is to be inserted.*

* * * * *

UNITED STATES PATENT AND TRADEMARK OFFICE

CERTIFICATE OF CORRECTION

PATENT NO. : RE 34,632

DATED : June 7, 1994

INVENTOR(S) : Berggren et al.

It is certified that error appears in the above-identified patent and that said Letters Patent is hereby corrected as shown below:

Column 1, line 17, change "way" to --ways--.

Column 2, line 52, change "I" to --1--.

Column 3, line 11, change "ever" to --even--.

Column 5, line 54, delete the second "of".

Column 6, line 36, change "cancave" to --concave--.

Column 6, line 59, change "we" to --are--.

Signed and Sealed this

Thirteenth Day of September, 1994

*Attest:*

Bruce Lehman

BRUCE LEHMAN

*Attesting Officer*

*Commissioner of Patents and Trademarks*